United States Patent [19]

Nelson, Jr.

[11] Patent Number: 4,676,778
[45] Date of Patent: Jun. 30, 1987

[54] LONG INTESTINAL CATHETER WITH SUMP

[76] Inventor: Richard L. Nelson, Jr., 112 Broadway, Wilmette, Ill. 60091

[21] Appl. No.: 923,474

[22] Filed: Oct. 27, 1986

[51] Int. Cl.$^4$ ............................................. A61M 25/00
[52] U.S. Cl. ...................................... 604/45; 604/101; 604/129
[58] Field of Search ...................... 604/43, 45, 54, 101, 604/129

[56] References Cited

U.S. PATENT DOCUMENTS

| | | | |
|---|---|---|---|
| 2,614,563 | 10/1952 | Devine | 604/45 |
| 2,854,982 | 10/1958 | Pagano | 604/101 |
| 2,930,378 | 3/1960 | Buyers | 604/45 |
| 3,314,430 | 4/1967 | Alley et al. | 604/45 |
| 3,426,759 | 2/1969 | Smith | 604/45 |
| 3,528,427 | 9/1970 | Sheridan | 604/45 |
| 4,368,739 | 1/1983 | Nelson | 604/54 |

FOREIGN PATENT DOCUMENTS 2454589 6/1975 Fed. Rep. of Germany ...... 604/101

OTHER PUBLICATIONS

Nelson, et al., Surgery, Gynecology and Obstetrics, Apr., 1985, vol. 160, pp. 369–372, "A New Tube for Simultaneous Gastric Decompression and Jejunal Alimentation".

Primary Examiner—Dalton L. Truluck
Attorney, Agent, or Firm—Marshall, O'Toole, Gerstein, Murray & Bicknell

[57] ABSTRACT

A long intestinal catheter is readily insertable into the small intestine via the nasogastric route. The tube aspirates the small intestine during the operative period, internally plicates the small intestine after surgery, and can aspirate the stomach and the small intestine during the post-operative period. The tube is self-sumping and avoids blockage or closure of any aspirating opening in the tube by the interior lining of the stomach or small intestine during aspiration.

12 Claims, 8 Drawing Figures

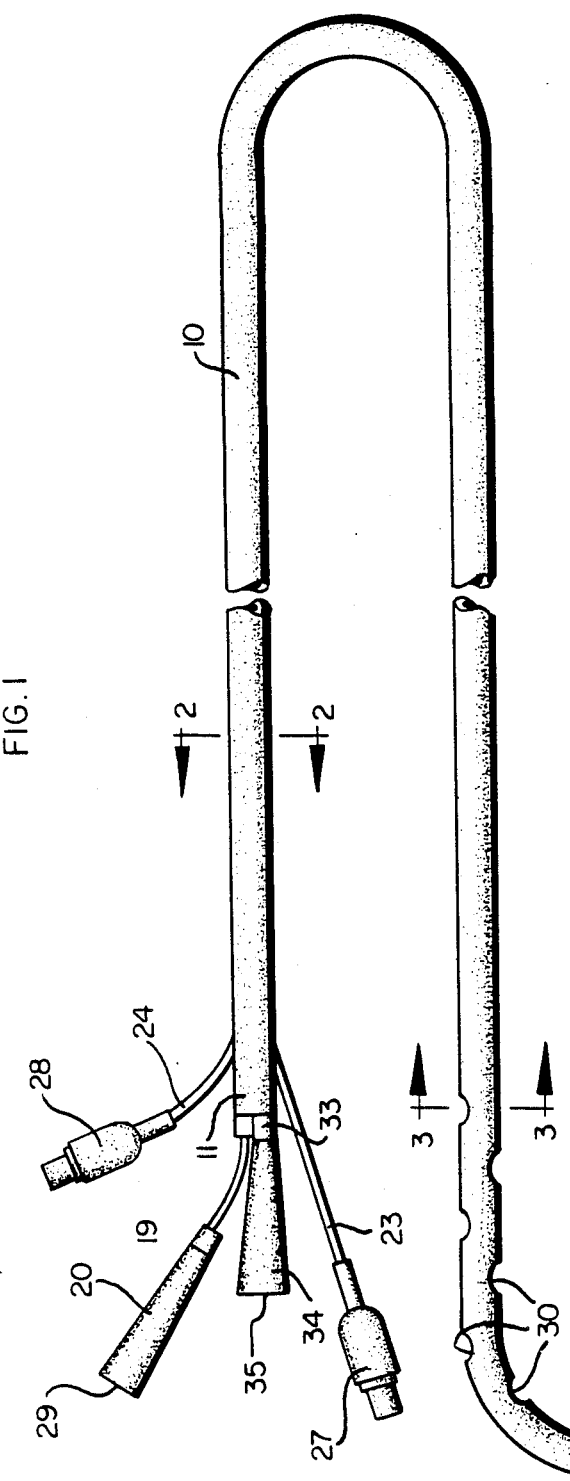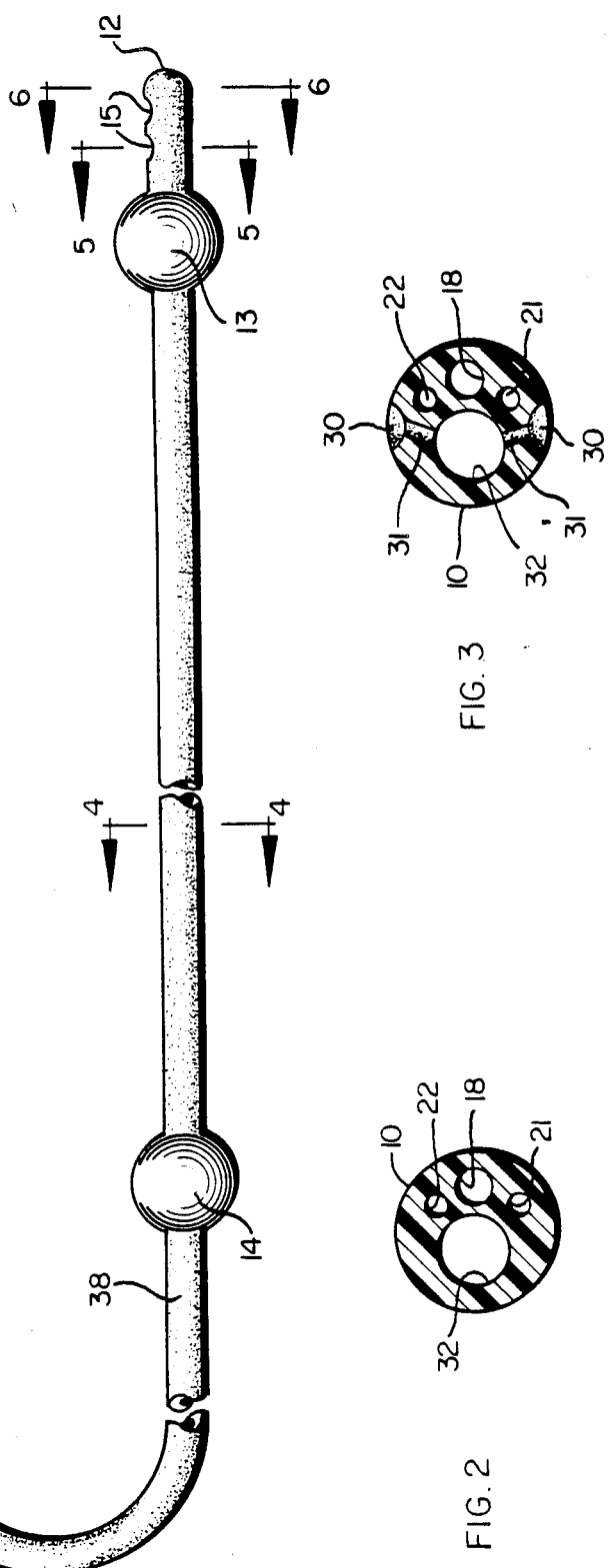

LONG INTESTINAL CATHETER WITH SUMP

BACKGROUND OF THE INVENTION

The present invention relates generally to intestinal catheters and more particularly to an intestinal catheter, inserted via the nasogastric route, for aspirating both the small intestine and the stomach.

The gastrointestinal tract comprises, in descending order from the mouth or nose, the esophagus, the stomach, the small intestine and the large intestine. The small intestine or bowel comprises, in descending order, the duodenum, connected to the stomach through an opening called the pylorus, the jejunum, which connects with the duodenum at a location identified by an adjacent ligament called the ligament of Treitz, and the ileum which in turn connects with the large bowel or colon.

Certain patients suffer from an obstruction in the small intestine. This obstruction is caused by scar tissue on the outside of the small intestine which constricts or squeezes the bowel causing the bowel upstream of the obstruction to become massively dilated, i.e., swollen or puffed up, while the bowel downstream of the obstruction remains normal sized. The scar tissue which causes the obstruction usually occurs following abdominal surgery, but it can occur from inflammation of the bowel. When the obstruction occurs following abdominal surgery, it may occur within any time from a few days to several years after the surgery. Many patients having such an obstruction require surgery in order to alleviate the problem. In such a case, the abdomen is opened and the scar tissue is cut away, thereby relieving the obstruction and allowing passage of bowel content normally downstream.

Incident to such surgery, it is desirable to aspirate or remove the contents of the small bowel upstream of the obstruction.

This may be accomplished by utilizing a long intestinal catheter of the type described in Nelson U.S. Pat. No. 4,368,739. Such a catheter is inserted into the gastrointestinal tract via the nasogastric route, and it is moved downstream through the small bowel towards the obstruction. The contents of the small bowel are aspirated upstream through the tube into the proximal or upstream end of the tube, located outside the nose of the patient and connected to an aspirator or source of suction.

When inserting the catheter via the nasogastric route, the downstream or distal end of the catheter is inserted, in sequence, through the nose, the esophagus, the stomach, the duodenum and then into the jejunum. Manipulation of the catheter through the duodenum is facilitated by the provision of a pair of inflatable balloons on a downstream portion of the catheter, as is described in more detail in Nelson U.S. Pat. No. 4,368,739 and in an article entitled "A New Long Intestinal Tube", Nelson, et al., *Surgery, Gynecology and Obstetrics*, October, 1979, Volume 149, Pages 581-582.

At the conclusion of the surgery, the catheter is worked further downstream through the small bowel to the distal end of the latter, and then, with the catheter in place through the entire length of the small bowel, it acts as a guide for plicating the small bowel into place within the abdomen. In other words, the emplaced catheter allows the small bowel to be readily placed into an arrangement of orderly folds or convolutions, within the abdomen, without the occurrence of kinking in the small bowel as it is arranged in the convoluted disposition. The prevention of kinking is important. Otherwise, a new obstruction could occur wherever a kink is located. The inherent rigidity of the catheter within the small bowel prevents the bowel from kinking.

When the abdomen is closed following surgery, the proximal or upstream end of the catheter remains in a position outside the body of the patient, adjacent the nose, and the downstream end remains in the small bowel. During this post-operative period (e.g. 8-10 days), the contents of the small bowel may be aspirated through the catheter. Thereafter, the tube can be removed through the nose.

During the post-operative period, it is oftentimes also desirable to be able to aspirate the contents of the stomach. In the recent past, this has sometimes been accomplished through a tube inserted via the nasogastric route and terminating in the jejunum. That part of the tube located in the jejunum contained openings for feeding liquid into the jejunum for nourishing the patient during the post-operative period. There were also openings in that part of the tube located in the stomach for aspirating the contents of the stomach. The tube included separate channels or lumens for the aspirating openings in the stomach and for the feeding openings in the jejunum. A tube of this type is described in an article entitled "A New Tube For Simultaneous Gastric Decompression and Jejunal Alimentation", Nelson et al., *Surgery, Gynecology and Obstetrics*, April, 1985, Vol. 160, Pages 369-372.

It is desirable, during the post-operative period, to be able to aspirate the contents of the small intestine as well as the contents of the stomach. A problem which can arise during aspiration of the small intestine or stomach is a plugging or closure of the aspirating openings by the interior lining of the stomach or small intestine which are drawn against the aspirating openings by the aspirating suction. Continuously applied suction resulted in this plugging occurring almost immediately. Most hospital wards and operating rooms have only continuous suction. In order to prevent plugging, it was necessary periodically to interrupt the suction manually or to employ a special device which intermittently opened and closed the suction valve. Another expedient that prevented the immediate and persistent plugging described above was to provide a suction break within the tube. This was accomplished by having a separate lumen connected to the suction lumen near the distal end of the tube and open to the atmosphere near the proximal end of the tube to admit air, thus creating a sump tube. See Alley et al U.S. Pat. No. 3,314,430.

SUMMARY OF THE INVENTION

There is provided in accordance with the present invention a single tube or catheter which performs all of the following functions: aspiration of the small bowel during the operative period; plication of the small bowel at the end of the operative period; aspiration of the small bowel during the post-operative period; and aspiration of the stomach during the post-operative period. Plugging during aspiration is prevented.

The catheter comprises a flexible tube having upstream and downstream ends. The tube contains four lumens, two of which are employed to inflate balloons at the downstream portion of the tube, for use in manipulating the tube through the small intestine.

The tube may be quickly and easily inserted into the jejunum by the nasogastric route. The tube has a length such that, when the downstream end of the tube is at the distal end of the small intestine, the upstream end of the tube extends outwardly through the nose. The tube has at least one aspirating opening at the downstream end of the tube for aspirating the small intestine. A first aspirating lumen in the tube, communicates with the aspirating opening for the small intestine and terminates at an upstream end adjacent the upstream end of the tube. The upstream end of this lumen may be connected to suction or it may be employed for venting the first aspirating lumen to the atmosphere.

The tube has additional aspirating openings for aspirating the stomach. A second aspirating lumen in the tube communicates with each of the additional aspirating openings and terminates at an upstream end adjacent the upstream end of the tube. The upstream end of the second aspirating lumen may be connected to suction or it may be employed for venting the second aspirating lumen to the atmosphere.

Located within the tube, downstream of the furthest downstream opening for aspirating the small intestine, is a channel connecting the first and second aspirating lumens.

When one of the aspirating lumens is connected to suction, the other aspirating lumen is left open to the atmosphere, and because of the channel connecting the two aspirating lumens, the aspirating lumen open to the atmosphere serves as a sump for the aspirating lumen connected to suction. This prevents the lining of the stomach or small intestine from blocking or closing the openings through which the aspirating operation is being conducted.

The arrangement described in the preceding paragraph also permits the stomach to be aspirated without aspirating the small intestine and vice versa.

As the catheter is advanced through the jejunum, it may perform the usual aspirating function heretofore performed by the prior art catheter described above. After the obstruction has been alleviated, the catheter of the present invention may be advanced to the distal or downstream end of the small intestine and used for internal plication of the small intestine.

That part of the tube which is employed to internally plicate the small intestine is located downstream of the furthest downstream of the aspirating openings employed to aspirate the stomach. None of the aspirating openings intended to aspirate the stomach are in any part of the gastrointestinal tract other than the stomach when the downstream end of the tube is at the distal end of the small intestine.

After the surgery has been completed and the abdomen closed, the proximal or upstream end of the catheter is allowed to remain in a disposition extending out from the nose of the patient, and, at the conclusion of the post-operative period the catheter may be removed merely by pulling it out through the nose.

Other features and advantages are inherent in the catheter claimed and disclosed or will become apparent to those skilled in the art from the following detailed description in conjunction with the accompanying diagrammatic drawings.

BRIEF DESCRIPTION OF THE DRAWINGS

FIG. 1 is a plan view of an embodiment of a catheter constructed in accordance with the present invention;

FIG. 2 is a sectional view taken along line 2—2 in FIG. 1;

FIG. 3 is a sectional view taken along line 3—3 in FIG. 1;

DETAILED DESCRIPTION

Figure 4:
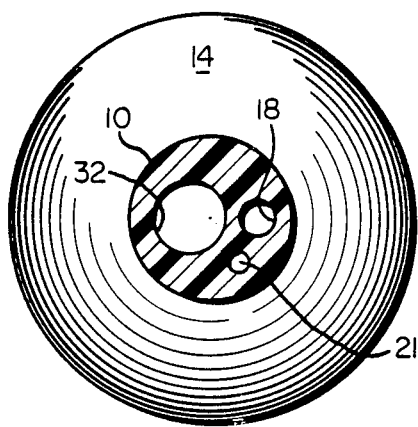
FIG. 4 is a sectional view taken along line 4—4 in FIG. 1.

Referring initially to FIG. 1, there is illustrated a catheter constructed in accordance with an embodiment of the present invention and comprising a flexible tube 10 having an upstream end 11 and a downstream end 12.

Surrounding tube 10 adjacent downstream end 11 is a first inflatable balloon 13, and surrounding tube 10 at a location upstream from first balloon 13 is a second inflatable balloon 14. Balloons 13 and 14 comprise structure manually manipulable to advance the catheter through the duodenum and into the jejunum of the small intestine during surgery. This is all described in greater detail in the aforementioned U.S. Pat. No. 4,368,739, and the disclosure therein is incorporated herein by reference.

The catheter is inserted into the small intestine via the nasogastric route, i.e. through the nose, the esophagus, the stomach and then into the small intestine. Tube 10 has a length such that, when downstream end 12 is at the distal end of the small intestine, upstream tube end 11 extends outwardly through the nose.

Located adjacent downstream end 12 of tube 10 are a pair of aspirating openings 15, 15 for aspirating the contents of the small intestine. Each opening 15 communicates through a respective channel 17 (FIG. 5) with a first aspirating lumen 18 which terminates at an upstream end portion 19 adjacent upstream end 11 of tube 10. Connected to upstream end portion 19 is a coupling 20 having an open end 29 for connecting lumen 18 to suction or for venting the lumen to the atmosphere.

Figure 5:
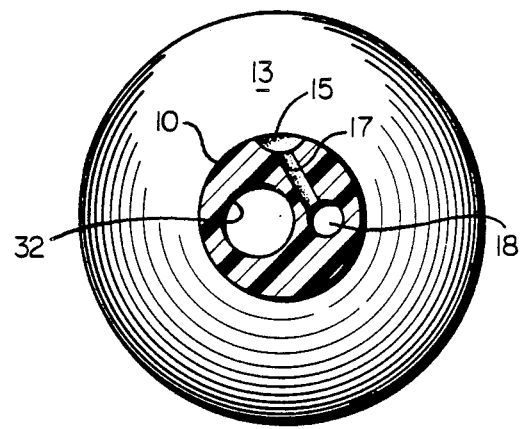
FIG. 5 is a sectional view taken along line 5—5 in FIG. 1.
Figure 6:
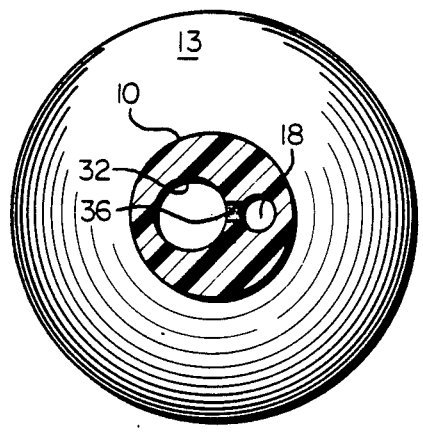
FIG. 6 is a sectional view taken along line 6—6 in FIG. 1.

In the embodiment of FIG. 5, aspirating openings 15, 15 are each in the form of a relatively shallow recess connected by channel 17 to lumen 18. In another embodiment, the location of opening 15 could be rotated 90° in a clockwise sense (as viewed in FIG. 5) and provided with a relatively deep recess extending all the way to, and communicating with, lumen 18. Similar structure can be used for the other aspirating openings 30, 30.

Figure 7:
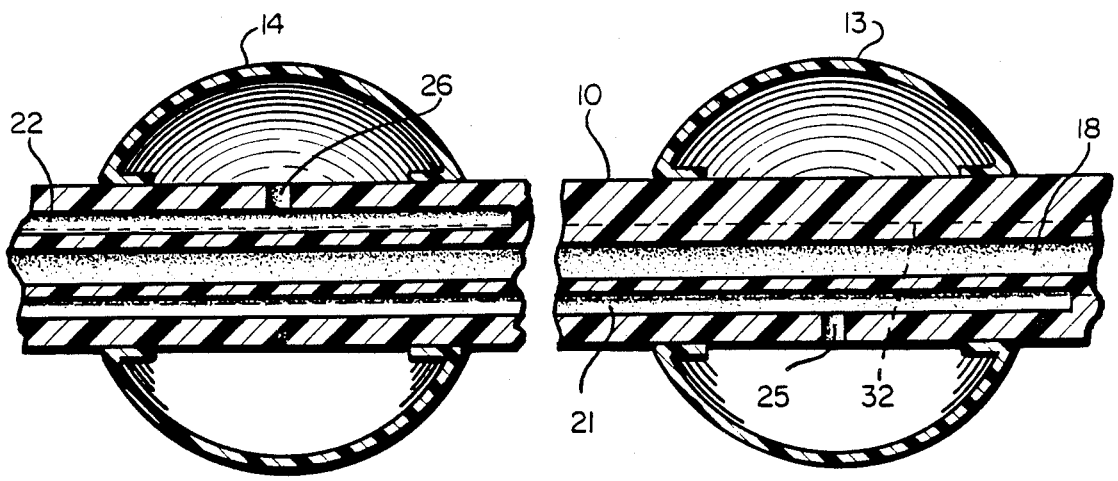
FIG. 7 is an enlarged, fragmentary, longitudinal sectional view.

Also located within tube 10 are a pair of balloon lumens 21, 22 (FIGS. 2–4 and 7) each comprising a conduit for introducing an inflating gas into a respective balloon 13 or 14. More particularly, each balloon lumen 21, 22 communicates with its respective balloon 13, 14 through a respective channel 25, 26 (FIG. 7), and each balloon lumen 21, 22 terminates at a respective upstream end portion 23, 24 adjacent upstream end 11 of tube 10 (FIG. 1). Connected to upstream end portions 23, 24 of balloon lumens 21, 22 are couplings 27, 28 for connecting a respective balloon lumen to a source of inflating gas.

The respective upstream end portions 19, 23, 24 of lumens 18, 21 and 22 are located outside of tube 10 adjacent the tube's upstream end 11.

As shown in Fi9. 1, tube 10 has additional aspirating openings 30, 30 for aspirating the stomach. Tube 10 has a length such that when downstream end 12 of tube 10 is at the distal end of the small intestine, substantially all of the additional aspirating openings 30, 30 are in the stomach.

Referring to FIG. 3, each additional opening 30 communicates through a corresponding channel 31 with a second aspirating lumen 32 terminating at an upstream end portion 33 (FIG. 1) connected to a coupling 34 having an open end 35 for connecting lumen 32 to suction or for venting lumen 32 to the atmosphere.

Figure 8:
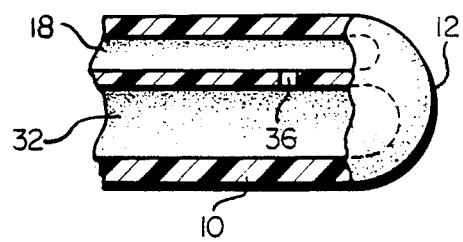
FIG. 8 is an enlarged fragmentary view, partially in section, of the distal end of the tube.

As shown in FIG. 8, the two aspirating lumens 18 and 32 extend almost to the downstream end 12 of tube 10. Connecting lumens 18 and 32, at a location adjacent the tube's downstream end 12, is a channel 36 positioned downstream of the furthest downstream aspirating opening 15. Channel 36, first aspirating lumen 18 and coupling 19 comprise structure for venting second aspirating lumen 32 to the atmosphere when lumen 32 is connected to suction via coupling 34. Similarly, channel 36, second aspirating lumen 32 and coupling 34 comprise structure for venting first aspirating lumen 18 to the atmosphere when lumen 18 is connected to suction via coupling 20. By venting one of the couplings 20, 34 to the atmosphere when the other coupling is connected to suction, one can use the catheter for aspirating the small intestine without aspirating the stomach, and vice versa.

The structure described in the preceding paragraph prevents openings 15, 15 from being plugged by the interior lining of the small intestine when the latter is being aspirated through lumen 18. Similarly, the same structure prevents openings 30, 30 from being plugged by the lining of the stomach when the stomach is being aspirated through lumen 32. This is because whenever a lumen 18 or 32 is employed in an aspirating operation it is vented to the atmosphere through a connection (channel 36) located downstream of the furthest downstream opening employed for aspirating purposes with that particular lumen.

Because one of the two aspirating lumens 18, 32 acts as a sump or vent to the atmosphere when the other lumen is employed in an aspirating operation, continuous suction can be employed without manually interrupting the suction or without employing a complicated automatic suction interrupting valve, and there will be no plugging of an aspirating opening by the lining of the small intestine or stomach.

Aspirating openings 15, 15 are used to aspirate the small intestine during the operative period. When the surgery has been completed, tube 10 is extended through the small intestine until the tube's downstream end 12 is located at the distal end of the small intestine, and a downstream tubular portion 38 of tube 10 is then employed to internally plicate the small intestine. Downstream tubular portion 38 is located downstream of the furthest downstream of the aspirating openings 30, 30.

During the post operative period, which lasts up to 14 days for example, there are times when aspiration of the stomach is desirable. With the catheter in place as described above, this is readily accomplished. When the tube's downstream end 12 is at its maximum distance of insertion (at the distal end of the small intestine), openings 30, 30 are all located in the stomach and are available for aspirating the stomach. At the same time, the tube remains positioned for internal plication of the small intestine.

For optimum plication of the small intestine, the downstream end 12 of the tube should be at the distal end of the small intestine. When thus disposed, the entirety of the small intestine is plicated on the tube.

As noted above, when the downstream end 12 of tube 10 is at the distal end of the small intestine, all of the aspirating openings 30, 30 are in the stomach. In order to accomplish this, the distance between downstream tube end 12 and the furthest downstream of aspirating openings 30, 30 should be in the range of about 60 to 84 inches (152-213 cm.). Preferably, this distance is about 72 inches (183 cm.). The tube has a total length, from upstream end 11 to downstream end 12 in the range of about 121-141 inches (307-358 cm.).

The required distance, between downstream tube end 12 and the furthest downstream opening 30, for maintaining all of the openings 30, 30 in the stomach when downstream tube end 12 is at the distal end of the small intestine, may vary from person to person depending upon whether the person has previously had part of the small intestine removed. However, for a given group of people, this distance will always be about 6 feet (183 cm.) plus or minus 12 inches (30.5 cm.). If it turns out that the tube is too long and the furthest upstream opening 30 is not in the stomach (but is in the esophagus), one may push tube 10 in a little further, and even if downstream tube end 12 is then a little past the distal end of the small intestine (i.e. in the colon) this would be acceptable.

On the other hand, if tube 10 is too short, and the furthest downstream opening 30 is in the small intestine when the tube's downstream end 12 is at the distal end of the small intestine, the tube can be retracted a little when aspiration of the stomach is desired. This may result in a loss of internal plication at the furthest downstream portion of the small intestine, but so long as about 90% of the small intestine is internally plicated by tube 10, this is still acceptable. Therefore, tube 10 should have a length such that, when the tube's downstream end 12 is located at a position constituting at least about 90% of the distance to the distal end of the small intestine, all of aspirating openings 30, 30 are in the stomach.

The foregoing detailed description has been given for clearness of understanding only, and no unnecessary limitations should be understood therefrom, as modification will be obvious to those skilled in the art.

I claim:

1. A catheter for nasogastric insertion into the small intestine, said catheter comprising:

a flexible tube having upstream and downstream ends;

means manually manipulable to advance said tube through the duodenum and into the jejunum of the small intestine;

said tube having a length such that when the downstream end of the tube is at the distal end of the small intestine, the upstream end of the tube extends outwardly through the nose;

said tube having at least one aspirating opening adjacent the downstream end of the tube for aspirating the small intestine;

a first aspirating lumen in said tube, communicating with said aspirating opening for the small intestine and terminating at an upstream end adjacent the upstream end of the tube;

said first aspirating lumen comprising means at its upstream end for connecting said lumen to suction or for venting said lumen to the atmosphere;

said tube having additional aspirating openings for aspirating the stomach;

said tube having a length such that when said downstream end of the tube is at the distal end of the small intestine, at least some of said additional aspirating openings are in the stomach;

a second aspirating lumen in said tube, communicating with each of said additional aspirating openings and terminating at an upstream end adjacent the upstream end of the tube;

said second aspirating lumen comprising means at its upstream end for connecting said lumen to suction or for venting said lumen to the atmosphere;

and channel means connecting said first and second aspirating lumens at a location downstream of the furthest downstream opening for aspirating the small intestine.

2. A catheter as recited in claim 1 wherein:

said channel means, said first aspirating lumen and said means for venting said first aspirating lumen to the atmosphere together comprise means for venting said second aspirating lumen to the atmosphere when the second aspirating lumen is connected to suction; and said channel means, said second aspirating lumen and said means for venting said second aspirating lumen to the atmosphere together comprise means for venting said first aspirating lumen to the atmosphere when the first aspirating lumen is connected to suction.

3. A catheter as recited in claim 1 and comprising:

means, including said channel means, for venting said first aspirating lumen to the atmosphere when the first aspirating lumen is connected to suction and for venting the second aspirating lumen to the atmosphere when the second aspirating lumen is connected to suction.

4. A catheter as recited in claim 1 and comprising:

means, including said first aspirating lumen and said first-recited aspirating opening, for aspirating the small intestine without aspirating the stomach;

and means, including said second aspirating lumen and said additional aspirating openings, for aspirating the stomach without aspirating the small intestine.

5. A catheter as recited in claim 1 wherein said flexible tube comprises:

a downstream tubular portion located downstream of the furthest downstream of said additional aspirating openings;

said downstream tubular portion comprising means for internally plicating the small intestine.

6. A catheter as recited in claim 1 wherein:

none of said additional aspirating openings are in any part of the gastrointestinal tract other than the stomach when the downstream end of the tube is at the distal end of the small intestine.

7. A catheter as recited in claim 1 wherein:

the distance between the downstream end of said tube and the furthest downstream of said additional aspirating openings is about 60 to 84 in. (152–213 cm.).

8. A catheter as recited in claim 7 wherein:

said distance is about 72 in. (183 cm.).

9. A catheter as recited in claim 1 wherein:

said tube has a total length of about 121 to 141 in. (307 to 358 cm.).

10. A catheter as recited in claim 1 wherein:

said tube has a length such that, when the downstream end of the tube is located at a position constituting at least about 90% of the distance to the distal end of the small intestine, all of said additional aspirating openings are in the stomach.

11. A catheter as recited in claim 1 wherein said manually manipulable means comprises:

a first inflatable balloon surrounding said tube adjacent said downstream end of the tube;

a second inflatable balloon surrounding said tube at a location spaced upstream from said first balloon;

and a pair of balloon lumens in said tube, each of said balloon lumens comprising means for introducing an inflating gas into a respective one of said balloons;

each of said balloon lumens communicating with its respective balloon and terminating at an upstream end adjacent the upstream end of said tube.

12. A catheter as recited in claim 1 wherein:

said tube length is such that substantially all of said additional aspirating openings are in the stomach when said downstream end of the tube is at the distal end of the small intestine.

* * * * *